United States Patent
Maeda

(10) Patent No.: US 6,589,483 B1
(45) Date of Patent: Jul. 8, 2003

(54) LIQUID DISPENSER

(75) Inventor: Yoshio Maeda, Tokyo (JP)

(73) Assignee: Cosmotec Co., Ltd, Tokyo (JP)

( * ) Notice: Subject to any disclaimer, the term of this patent is extended or adjusted under 35 U.S.C. 154(b) by 100 days.

(21) Appl. No.: 09/621,497

(22) Filed: Jul. 21, 2000

(30) Foreign Application Priority Data

Jul. 23, 1999 (JP) ............................................ 11-208875

(51) Int. Cl.$^7$ .............................. B01L 3/02; B01L 9/00; G01N 1/10; G01N 1/14; G01N 35/10; G01N 1/00; G01F 11/04; G01F 11/06

(52) U.S. Cl. ........................ 422/100; 422/104; 436/180; 73/863.32; 73/863.52; 73/863.54; 73/864; 73/864.01; 73/864.11; 73/864.13; 73/863.16; 73/863.17; 73/863.24; 73/863.25; 73/863.31; 222/249; 222/250

(58) Field of Search ........................... 422/100, 99, 104; 73/863.32, 863.52, 863.54, 864, 864.01, 864.11, 864.13, 864.16, 864.17, 864.24, 864.25, 864.31; 222/249, 250; 436/180

(56) References Cited

U.S. PATENT DOCUMENTS

| 3,568,735 A | * | 3/1971 | Lancaster |
| 3,650,306 A | * | 3/1972 | Lancaster |
| 4,158,035 A | * | 6/1979 | Haase et al. |

(List continued on next page.)

FOREIGN PATENT DOCUMENTS

| EP | 0210014 | 1/1987 |
| EP | 1 070 540 A2 | 1/2001 |
| JP | 7-244052 A | 9/1995 |
| JP | 8-285854 A | 11/1996 |
| JP | 10-263421 A | 10/1998 |

OTHER PUBLICATIONS

"Tango Liquid Handling System" brochure, Robbins Scientific Corporation, 2000.
CCS Packard "Platetrak™Creative Solutions for Automated Microplate Processing" brochure, 1998.
CCS Packard "Platetrak™Automated Microplate Handling System" brochure, 1999.
CCS Packard MultiPosition Dispense Module Automated 96– and 384–channel Pipettor brochure, 2000.
"EDR384S/96S Pipetting Workstation" brochure, Labcyte, Dec., 2000.
"384/96S Well Automatic Pipettor" brochure, Labcyte, Dec., 2000.
"JOBI–Well Systems & Accessories" brochure, updated Nov. 1998, Jenoptik Bioinstruments GmbH.
"Apricot Designs" brochure, PerkinElmer Life Sciences, 2000.
Matrix Technologies Corporation: Products: "Automation".

*Primary Examiner*—Jill Warden
*Assistant Examiner*—Brian R Gordon
(74) *Attorney, Agent, or Firm*—Wolf, Greenfield & Sacks, P.C.

(57) ABSTRACT

A liquid dispenser characterized by a dispensing head which is movable upward and downward as a whole and comprises a plurality of plungers supported by a plunger plate, drive means for moving the plunger plate upward and downward, a plurality of cylinders in which the plungers slidably fit, and a plurality of nozzles arranged at the lower ends of the cylinders and having configurations adapted to engage airtightly with holes for holding specific dispensing tips, the plurality of nozzles being supported by a single nozzle holder, which is built to be detachable from said dispensing head. According to the invention, only the nozzle holder that support nozzles has to be replaced with another holder conforming to dispensing tips of different dimensions. The arrangement facilitates the replacement and make the dispenser available at lower cost.

15 Claims, 9 Drawing Sheets

U.S. PATENT DOCUMENTS

| | | | |
|---|---|---|---|
| 4,215,092 A | * | 7/1980 | Suovaniemi et al. |
| 4,444,062 A | * | 4/1984 | Bennett et al. |
| 4,779,467 A | * | 10/1988 | Rainin et al. |
| 4,824,642 A | | 4/1989 | Lyman et al. |
| 5,055,263 A | * | 10/1991 | Meltzer |
| 5,061,449 A | | 10/1991 | Torti et al. |
| 5,104,621 A | | 4/1992 | Pfost et al. |
| 5,439,649 A | * | 8/1995 | Tseung et al. |
| 5,470,538 A | * | 11/1995 | Lind |
| 5,497,670 A | | 3/1996 | Carl |
| 5,525,302 A | | 6/1996 | Astle |
| 5,642,816 A | * | 7/1997 | Kelly et al. |
| 5,660,792 A | | 8/1997 | Koike |
| 5,772,962 A | * | 6/1998 | Uchida et al. |
| 5,827,745 A | * | 10/1998 | Astle |
| 5,915,284 A | * | 6/1999 | Meltzer et al. .......... 73/864.17 |
| 5,988,236 A | * | 11/1999 | Fawcett |
| 6,006,800 A | * | 12/1999 | Nakano |
| 6,116,099 A | * | 9/2000 | Carl ........................ 73/863.32 |
| 6,132,582 A | * | 10/2000 | King et al. |
| 6,182,719 B1 | * | 2/2001 | Yahiro |
| 6,258,324 B1 | * | 7/2001 | Yiu |
| 6,326,212 B1 | * | 12/2001 | Aoki ............................. 222/1 |
| 6,399,024 B1 | * | 6/2002 | Bevirt et al. ................ 422/100 |
| 6,415,669 B1 | * | 7/2002 | Carl ........................ 73/864.14 |
| 2002/0009391 A1 | * | 1/2002 | Marquiss et al. |
| 2002/0064887 A1 | * | 5/2002 | Shalon et al. ............... 436/180 |

* cited by examiner

LIQUID DISPENSER

This application claims priority from Japanese Application No. 11-208875, filed Jul. 23, 1999, the entire contents of which are incorporated herein by reference.

BACKGROUND OF THE INVENTION

1. Field of the Invention

This invention relates to a liquid dispenser for liquid reagents, liquid samples and the like and, more specifically, to a holder-exchanger of such a dispenser for holding or replacing its dispensing tips.

2. Prior Art

In hospitals and various other institutions where blood test, immunological examination, chemical reaction, and other tests are carried out, it is customary that the blood, sample, reagent, or other object to be tested (hereinafter collectively called "liquid") is simultaneously distributed in predetermined amounts among a number of wells, cuvettes, or other small containers (hereinafter simply called "wells") using as many dispensing tips.

FIGS. 1 to 3 illustrate a liquid dispenser embodying the present invention. Except the mechanism for holding and replacing dispensing tips, the construction of the apparatus is known to the art. With this in view, a liquid dispenser of the prior art will now be explained with reference to the drawings.

FIG. 1 is a front view of the liquid dispenser, FIG. 2 is a side view, and FIG. 3 is a plan view of a stage assembly of the dispenser. The apparatus includes a horizontal base 1 and a housing frame of upright support 2. The horizontal base 1 carries an X stage 3 movably in the X direction, and the X stage 3 supports thereon a Y stage 5 movably in the Y direction. The Y stage 5 in turn carries, by means of a frame plate 7, a tip rack 9 having an array of holes (in 8 rows and 12 columns) arranged in order to hold a number of tips, at least one plate 11 having holes to support a number of wells in an equidistantly spaced arrangement of the same number, and a reagent or wash tank 13 holding a reagent or wash as the case may be. The X and Y stages 3, 5 can be driven independently of each other by an X-axis drive motor 15 or Y-axis drive motor 17 at a command from a control console.

The upright support 2 supports a Z-axis-movable dispensing head 19, which carries plungers 21 and cylinders 23 in the same numbers and at the same intervals as the holes of the tip rack 9 and plate 11. Tips 100 or 102 (usually either type, although two types are shown here) are fitted to nozzles that constitute the lower ends of the cylinders 23. The dispensing head 19 is driven as a whole in the Z-axis direction by a Z-axis drive motor 27, and the plungers 21 are driven by an S-axis motor 79.

In operation, the X and Y stages 3, 5 are first driven to align the tip rack 9 to the nozzles of cylinders 23, the dispensing head 19 is lowered in the Z-axis direction until the nozzle tips are fitted airtightly in the bores at the upper ends of dispensing tips 100 or 102 so that all the tips 100 or 102 are held by the nozzles, and then the dispensing head 19 is moved up. Next, the reagent tank 13 is aligned just below the nozzles holding the tips 100 or 102, the dispensing head 19 is lowered, bringing the lower ends of the dispensing tips 100 or 102 into the reagent tank 13, the plungers 21 are moved upward to draw by suction predetermined amounts of the reagent, and thus the dispensing head 19 is raised. Then the plate 11 is brought in place under the nozzles holding the dispensing tips 100 or 102, the dispensing head 19 is lowered to position the tips 100 or 102 immediately above the wells containing the sample (blood or the like). Finally, the plungers 21 are forced downward to dispense the reagent into the sample wells.

The nozzles of the prior art constitute the lower ends of the cylinders, and the combinations of many cylinders and plungers arranged in an orderly manner are supported by a single supporting block. The amount to be dispensed depends on the size of the tips, and the outside diameter of the nozzles to fit in the holes at the ends of the tips must be changed in accordance with the dispensing amount. To meet this requirement, it has been common with conventional dispensers to provide a variety of support blocks that hold the plunger-cylinder combinations having nozzles designed for particular amounts to be dispensed and replace the whole unit of support block when required.

The necessity of providing a plurality of dispensing blocks, each of which having a number of plunger-cylinder combinations with nozzles carried by a support block, for different sizes of nozzles has made the dispensers expensive because their dispensing blocks call for high precision in manufacture. Moreover, the replacement of dispensing blocks is cumbersome and not easy.

SUMMARY OF THE INVENTION

The present invention solves the problems of the prior art by providing a dispenser in which nozzles are separated from cylinders and are supported by a common block as a nozzle block which alone can be replaced with another one when the necessity arises.

Thus the invention provides a liquid dispenser characterized by a dispensing head which is movable upward and downward as a whole and comprises a plurality of plungers supported by a plunger plate, drive means for moving the plunger plate upward and downward, a plurality of cylinders in which the plungers slidably fit, and a plurality of nozzles arranged at the lower ends of the cylinders and having configurations adapted to engage airtightly with holes for holding specific dispensing tips, the plurality of nozzles being supported by a single nozzle holder, which is built to be detachable from said dispensing head.

According to the invention, only the nozzle holder that support nozzles has to be replaced with another holder conforming to dispensing tips of different dimensions. The arrangement facilitates the replacement and make the dispenser available at lower cost.

The nozzles preferably have an annular extended head each and are loosely fitted in the support block, simply as inserted from above into the block. They are fitted in the holes at the upper ends of the dispensing tips by self-aligning and thereby achieve positive airtight engagement with the tips.

In a preferred form of the invention, an elastic seal plate such as of silicone rubber having openings aligned to the bores of the nozzles and cylinders is sandwiched between the upper surface of the nozzle holder and the plunger-cylinder block, whereby airtight fluid communication is easily established between the nozzles and cylinders.

In another preferred form of the invention, the means for attaching and detaching the nozzle holder in a predetermined point comprises vertical clamp plates having clamps adapted to be engaged with lower edges of the nozzle holder, elastic members that normally bias the clamp plates upward, and means for pressing the clamp plates downward against the urgings of the elastic members. The means for pressing the clamp plates downward may be a plunger plate and means for driving it. Once the clamp plates are forced downward, the nozzle holder descends too under its own weight to the point where it can be pulled off horizontally to replace with a nozzle holder carrying nozzles of a different size.

In a further preferred form of the invention, an eject plate is located under the nozzle holder to remove all dispensing tips simultaneously from the nozzles. The eject plate has a plurality of holes to allow the nozzles to extend through them with tip-fitting ends of the nozzles protruding beyond the bottom of the eject plate. The diameter of the holes of the eject plate is smaller than the outside diameter of the upper ends of the dispensing tips. The eject plate, when forced downward by the bottom surfaces of the clamps of clamp plates, can simultaneously release and remove all tips simultaneously from the nozzles. The plate is normally biased toward the nozzle plates by springs provided on the nozzle holder. As an alternative, the eject plate may be pressed downward by means other than the clamp plates.

DESCRIPTION OF THE PREFERRED EMBODIMENT

Now the present invention will be more fully described below in connection with an embodiment thereof.

Figure 1:
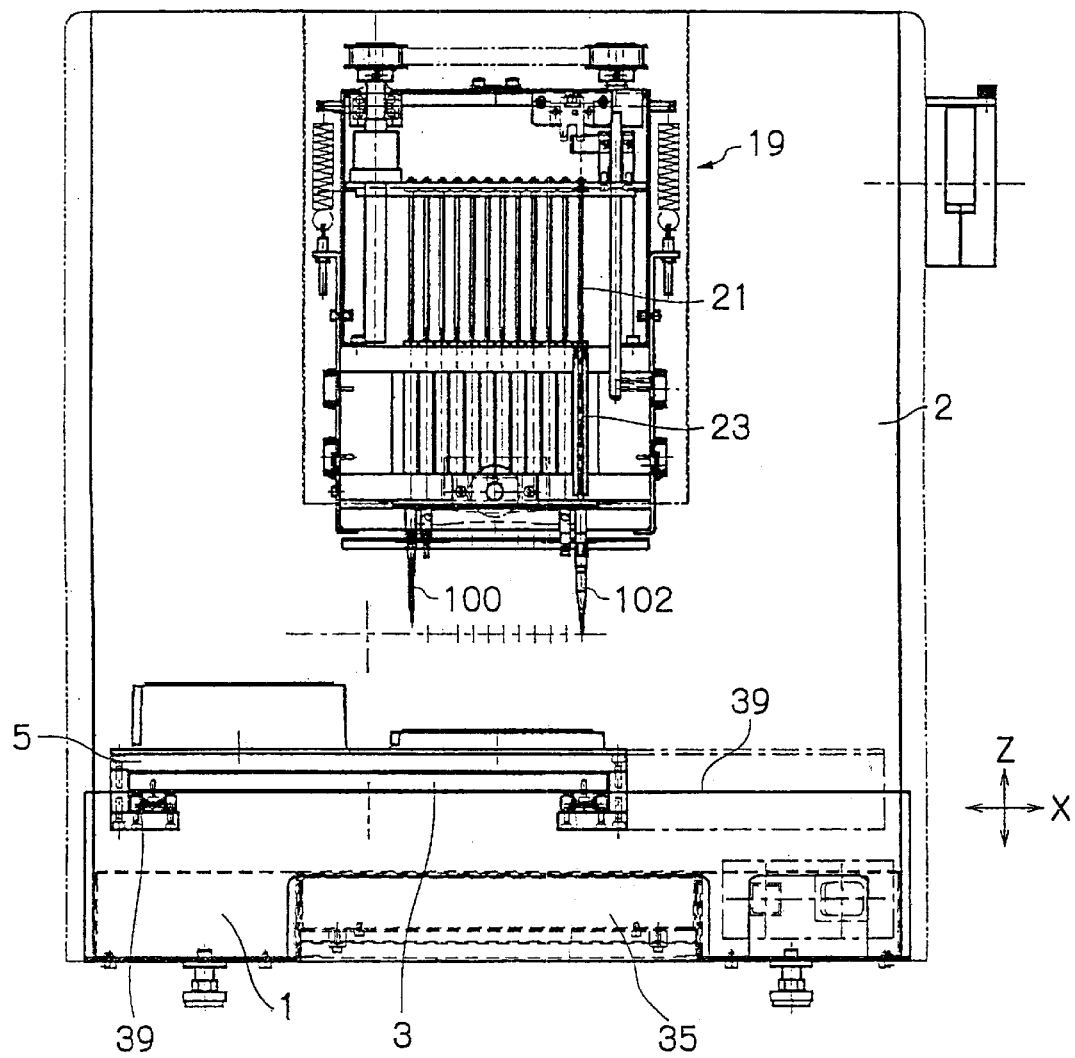
FIG. 1 is a front view of a liquid dispenser embodying the present invention.
Figure 2:
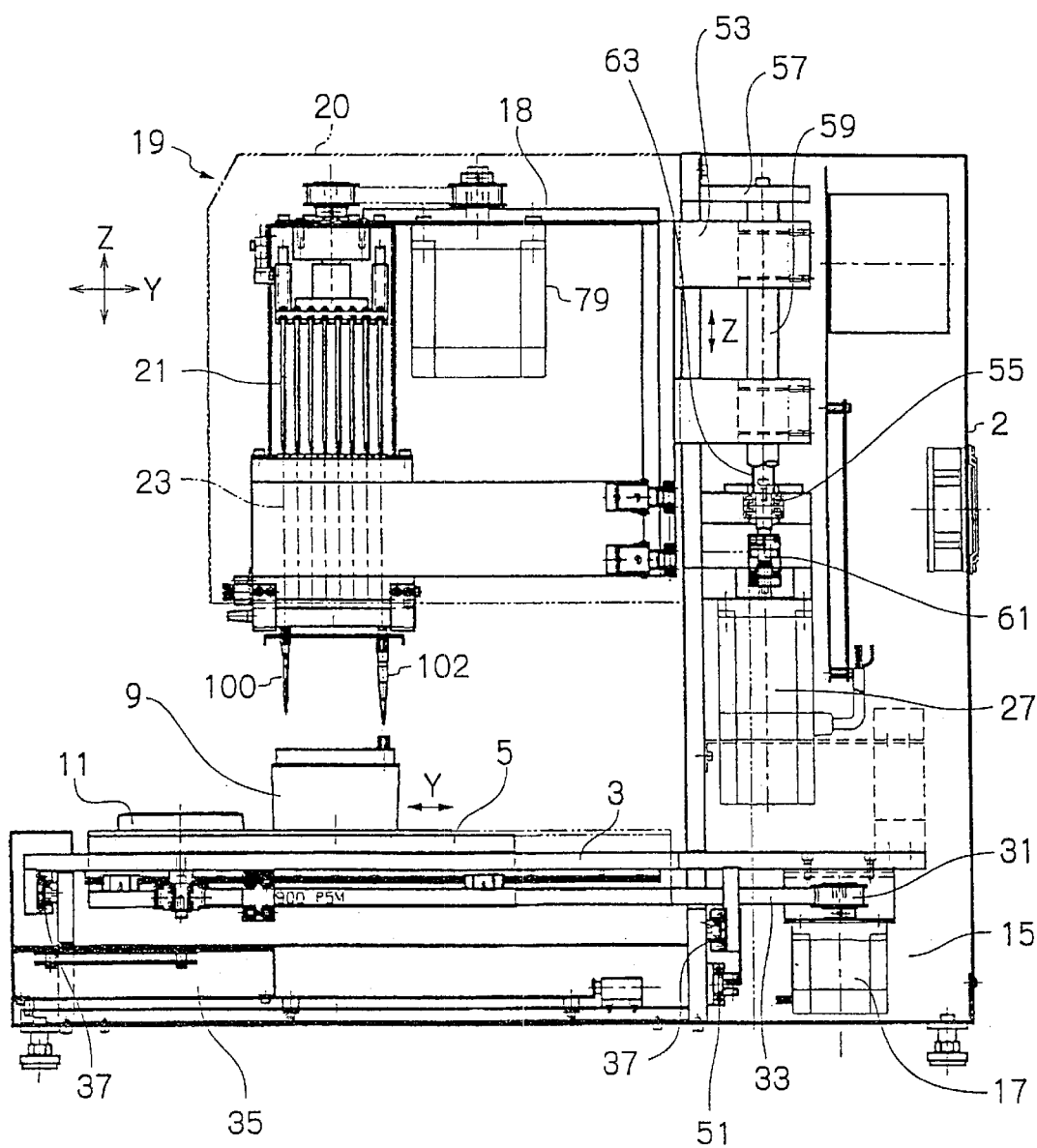
FIG. 2 is a right side view of the liquid dispenser of the invention.
Figure 3:
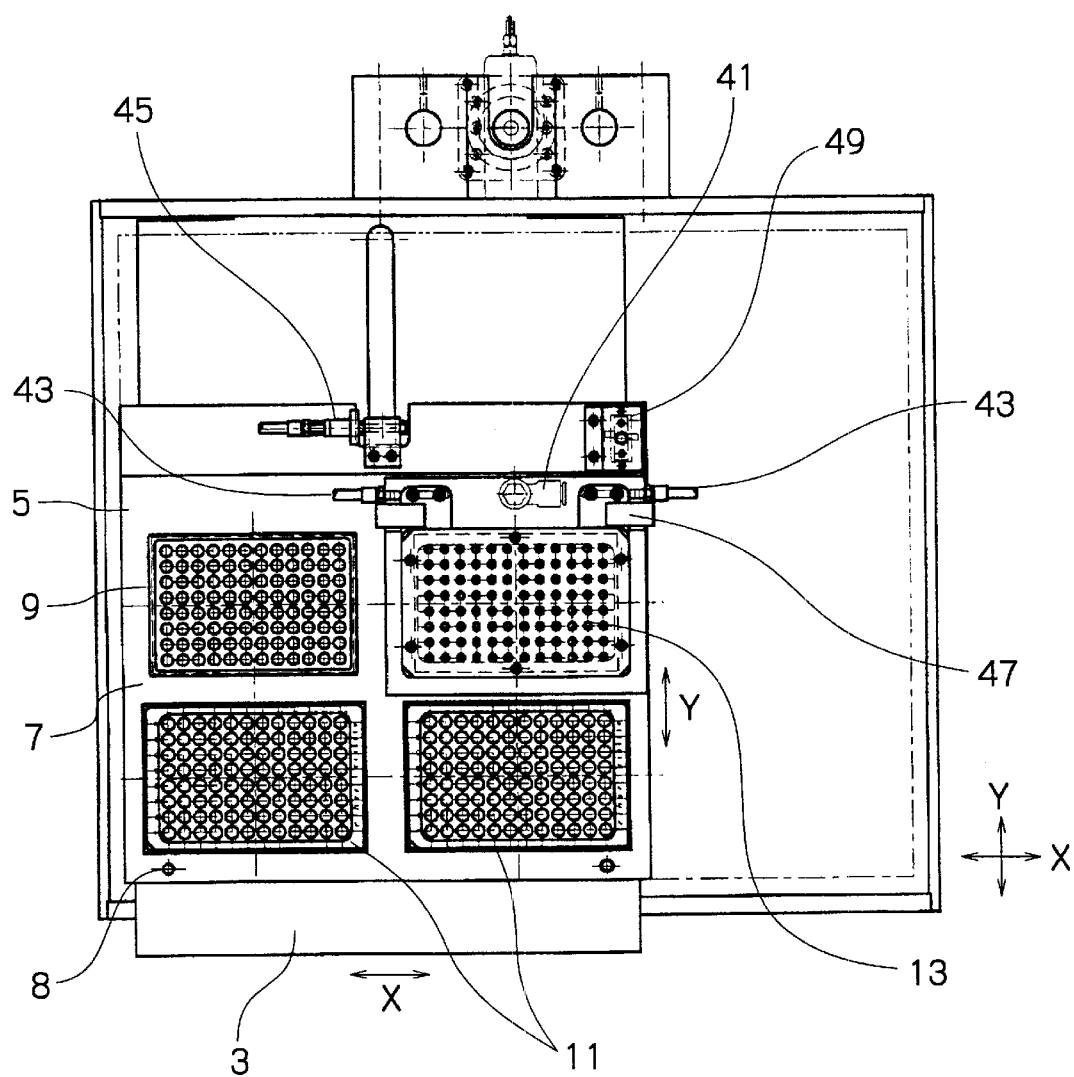
FIG. 3 is a plan view of a stage assembly of the dispenser according to the invention.

FIGS. 1 to 3 illustrate the general construction of a liquid dispenser embodying the invention, which is characterized by a dispensing head 19 having a mechanism for holding and replacing dispensing tips.

Figure 4:
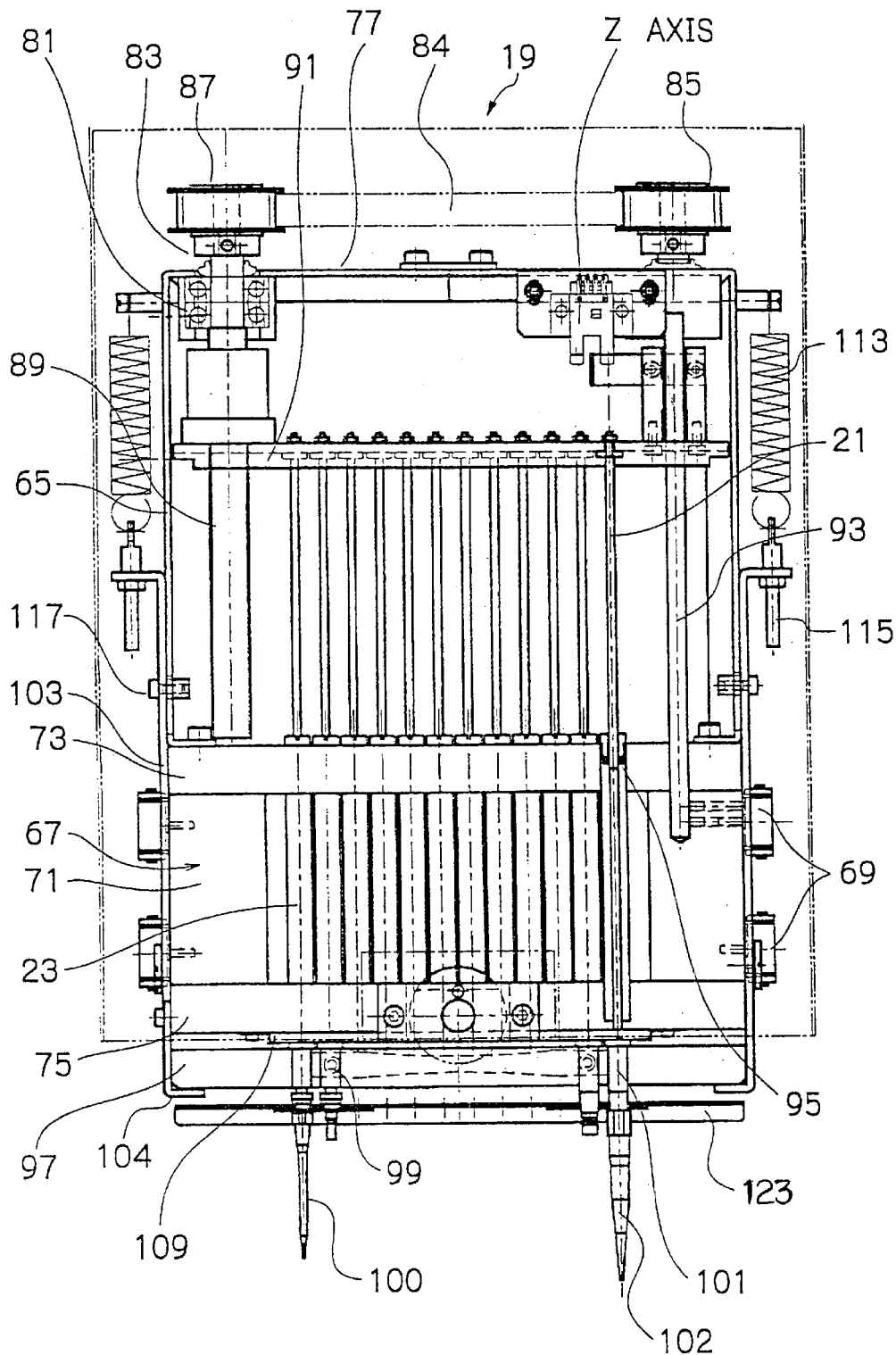
FIG. 4 is a front view of a dispensing head of the dispenser according to the invention.
Figure 5:
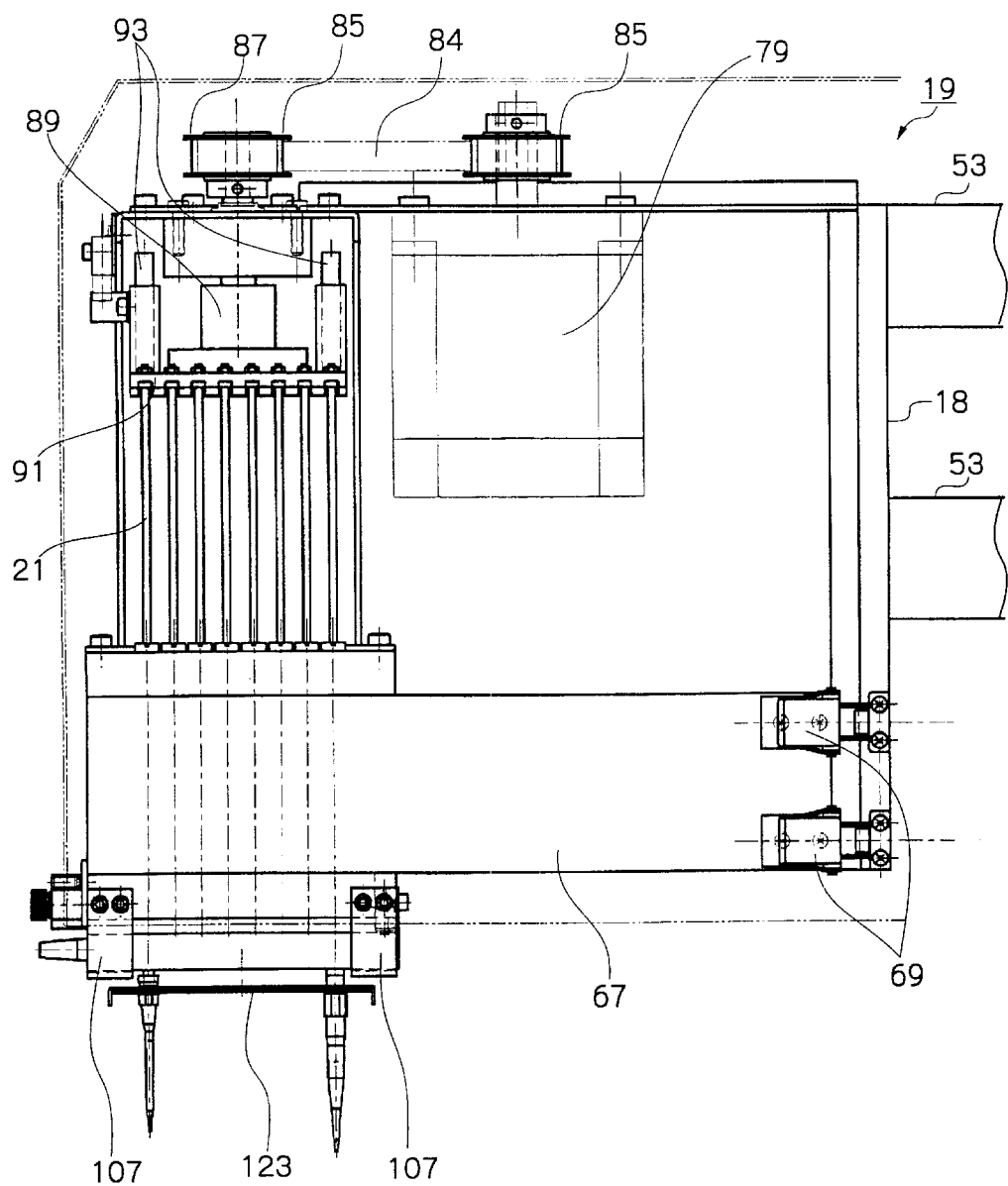
FIG. 5 is a right side view of the dispensing head of the dispenser, with the omission of a bracket.
Figure 6:
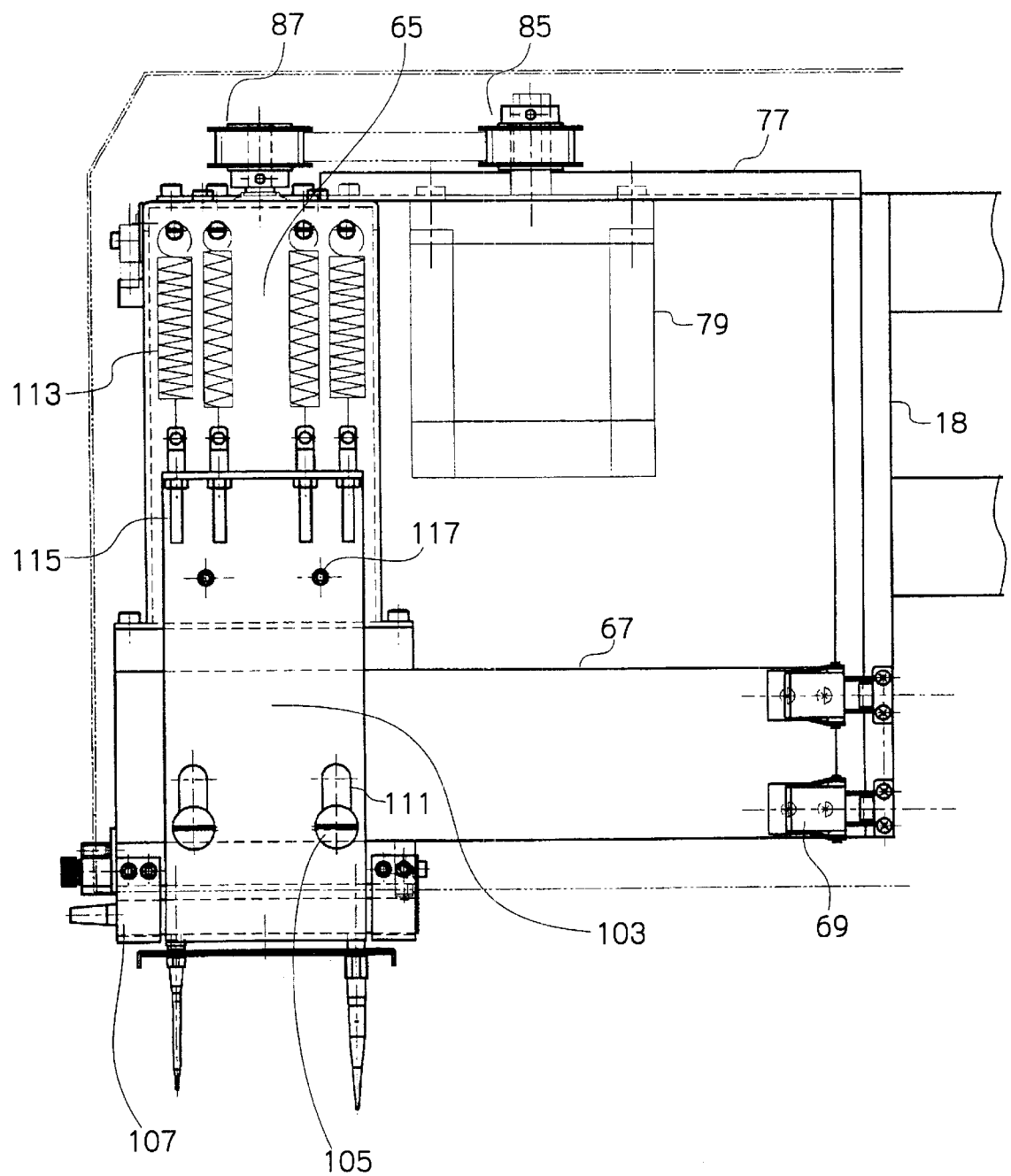
FIG. 6 is a right side view of the dispensing head, with the bracket attached.
Figure 7:
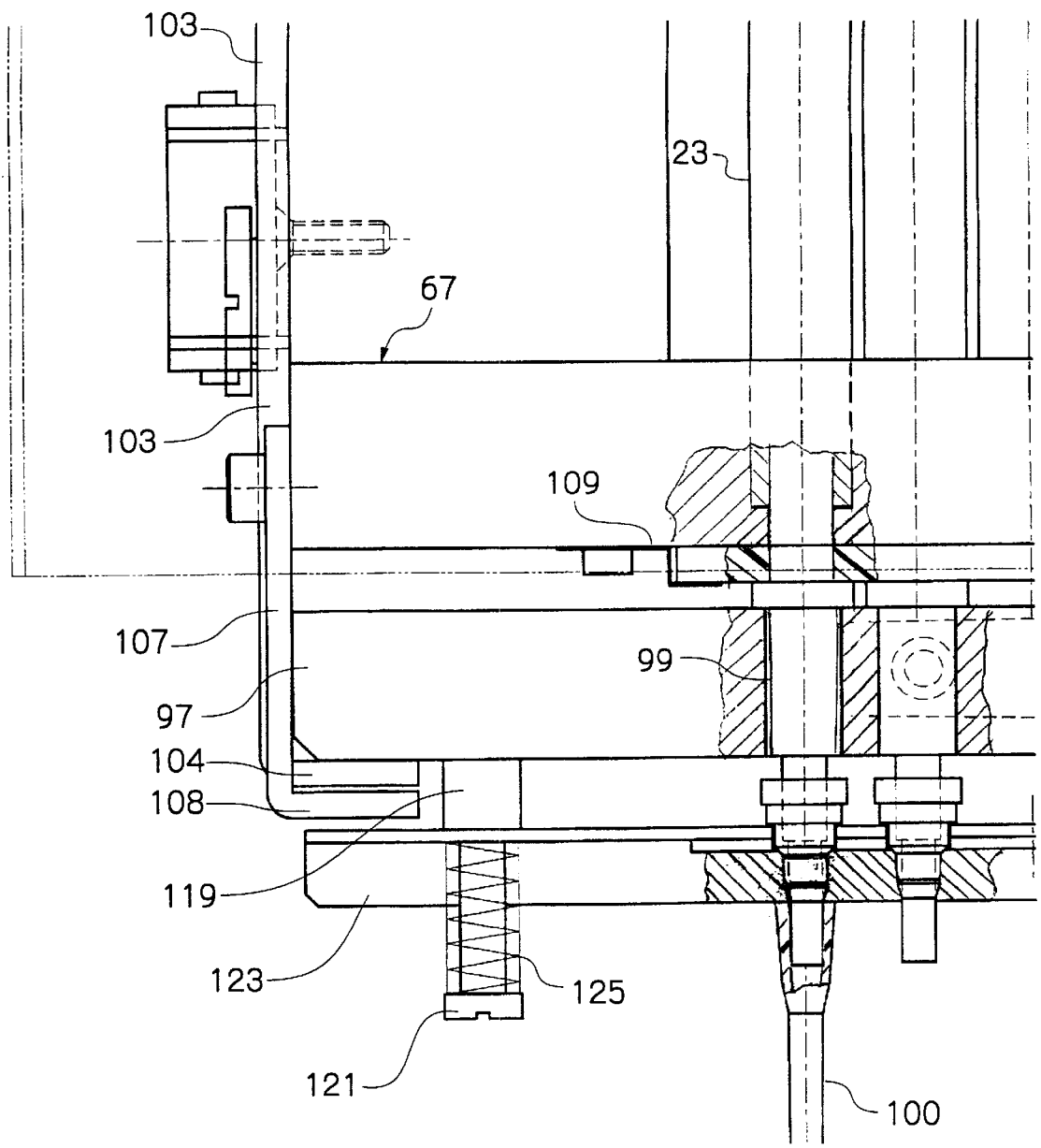
FIG. 7 is an enlarged front view of the essential parts of the dispending head.
Figure 8:
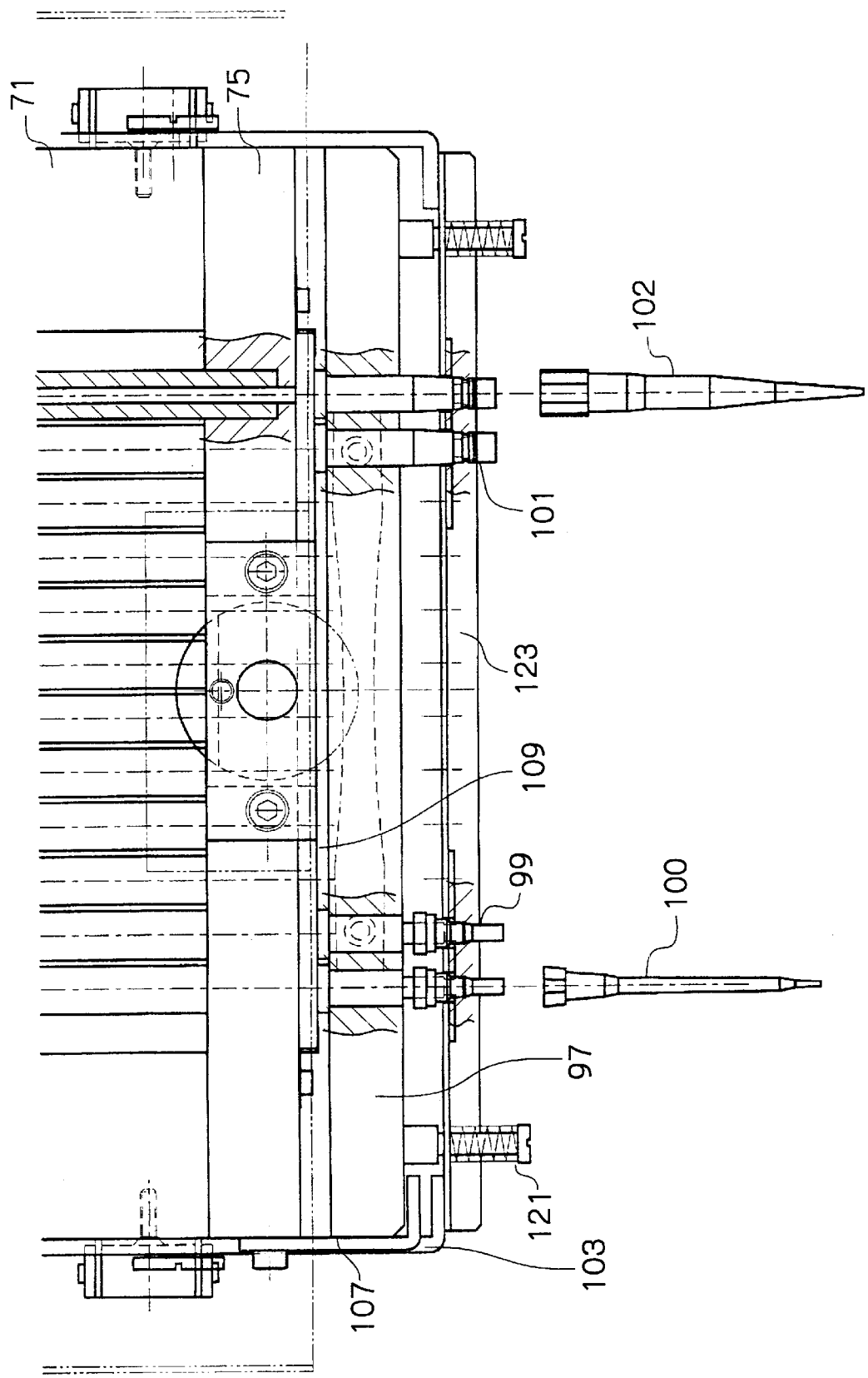
FIG. 8 is a front view of the essential parts associated with the operation of an eject plate in accordance with the invention.

FIGS. 4 to 6 are enlarged views of the dispensing head 19. Essential parts of the head 19 are shown in FIGS. 7 and 8.

FIG. 1 is a front view of the liquid dispenser, FIG. 2 is a side view, and FIG. 3 is a plan view of a stage assembly. The liquid dispenser includes a horizontal base 1 and a housing frame of upright support 2. The horizontal base 1 carries an X stage 3 which is made movable in the X direction by X-axis linear guides 37, and the X stage 3 supports thereon a Y stage 5 which is made movable in the Y direction by Y-axis linear guides 39 mounted on the X stage. The Y stage 5 carries thereon a frame plate 7 detachably secured in place with frame guide pins 8. The frame plate 7 in turn carries a tip rack 9 (see FIG. 9) having an array of holes (e.g., in 8 rows and 12 columns as shown) arranged in order to hold a number of tips 100 or 102, at least one plate 11 having holes to support a number of wells in an equidistantly spaced arrangement of the same number, and a reagent or wash tank 13 holding a reagent or wash as the case may be. There are also provided a feedwater inlet 41 for the wash, drain pipes 43, a drain pipe joint 45, a liquid level sensor 47, a liquid level sensor connector 49, etc. Those components have nothing to do with the subject of the present invention, and their detailed description is omitted.

The X stage 3 is driven in the X-axis direction, in response to a control signal received from a control console through a controller 35, by an X-axis drive motor 15 with a pulley 31 and a timing belt 33. Similarly, the Y stage 5 is driven independently of the X stage, in response to a control signal from the control console through the controller 35, by a Y-axis drive motor 17 with a pulley. The position of the X stage 3 is detected by an X-axis sensor 51. A Y-axis sensor (not shown) functions likewise.

The upright support 2 holds up a dispensing head 19 movably in the Z-axis direction. The dispensing head 19 has a frame 18 supported by a pair of linear bearings 53 vertically spaced apart and arranged in tandem. The linear bearings 53 are slidably guided in the Z-axis (vertical) direction by a pair of shaft-retaining plates 57 (only the upper one is shown) which too are vertically spaced apart and secured in tandem to the upright support 2. A Z-axis motor 27, mounted in the support frame 2, drives the linear bearings 53 in the Z-axis direction via a coupling 61 and a ball screw 63 retained in position by a bearing 55.

The construction of the dispensing head 19 will now be described with reference to FIGS. 4 to 6. FIG. 4 is a front view, FIG. 5 is a right side view with the omission of a vertical bracket 65, and FIG. 6 is a right side view with the bracket 65. A cylinder block 67 is secured with clamps 69 to the frame 18 of the dispensing head 19. On both front sides of the cylinder block 67, vertical brackets 65 are supported by a horizontal bracket 77 fixed to the frame 18. As shown in FIG. 4, the cylinder block 67 comprises two side blocks 71 and upper and lower blocks 73, 75 having am array of openings in a regular pattern to receive and support cylinders 23. The upper block 73 supports the upper ends of the cylinders 23 and the lower block 75 supports the lower ends.

Moreover, in the frame 18 of the dispensing head 19 is mounted an S-axis motor 79. The term S axis as used herein means the axis for motion in the vertical direction, as distinguished from the Z axis. The frame 18 also carries the horizontal bracket 77, which in turn supports a vertical rotating shaft 83 through bearings 81. The shaft is caused to rotate by the S-axis motor 79 through a pulley 85, timing belt 84, and pulley 87. The rotating shaft 83 has a ball screw 89, which bears up a horizontal plunger plate 91. The ball screw 89 changes the rotation of the shaft to a movement in the S-axis (vertical) direction and moves the plunger plate 91 upward and downward. The plunger plate 91 is fixed to guide shafts 93, which slide along guides secured to the frame 18 and through guide holes formed in the cylinder block to guide the plunger plate 91 vertically. To the plunger plate 91 are fixed the upper ends of a number of plungers 21 that fit in corresponding bores of cylinders 23. The lower ends of the plungers 21 fit in the upper ends of the cylinders 23 and the both ends are airtightly joined with seals 95.

In operation, the S-axis motor 79 is started and its power is transmitted through the pulley 85, timing belt 84, pulley 87, and rotating shaft 83 to rotate the ball screw 89, whereby the plunger plate 91 is driven downward or upward. The plungers 21 move into or out of the cylinders 23 a predetermined distance to draw a predetermined amount of air by suction or discharge it each. In this manner air can be introduced into or forced out of tips 100 or 102 by nozzles 101 so that a given liquid can be accurately dispensed in equal, predetermined amounts as will be explained in detail later.

Figure 9:
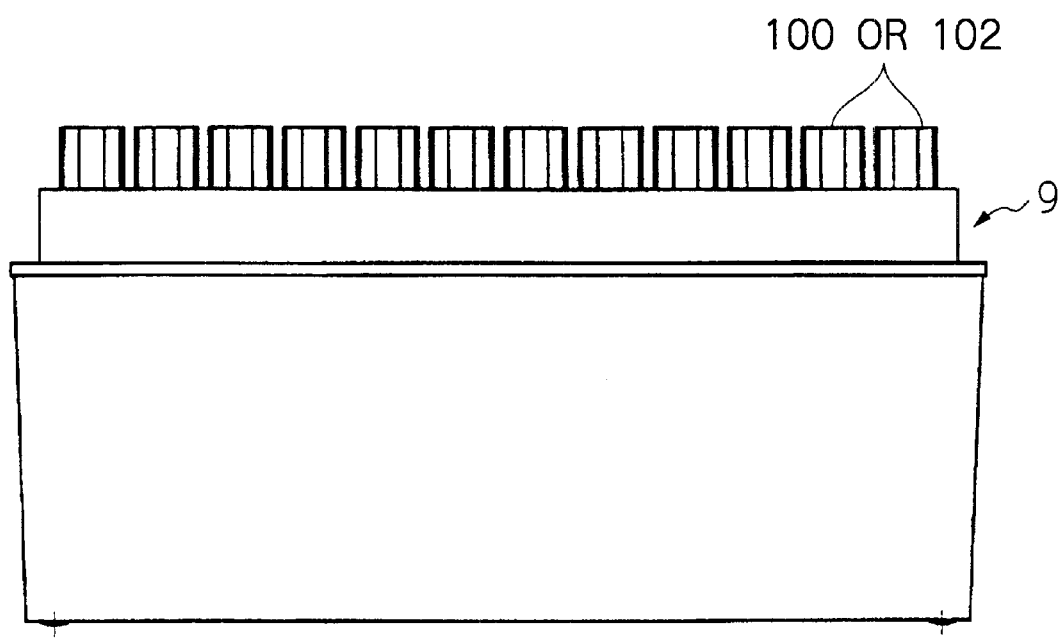
FIG. 9 is a schematic front view of dispensing tips and a tip rack supporting them.

The features of the invention will be described below in connection with FIGS. 7 and 8, in addition to FIGS. 4 to 6. Under the cylinder block 67, there is located a nozzle holder 97 which has a number of holes supporting an array of (small) nozzles 99 or (large) nozzles 101, preferably fitting loosely, in an arrangement corresponding to the cylinders. Loosely received in the holes, the nozzles have allowances to move slightly for a proper airtight fit when their ends are engaged with the upper end openings of tips. In the absence of the allowances, some of the many tips could fail to fit properly and be left unengaged in the rack 9 (FIGS. 3 and 9). The nozzles 99 or 101 have an annular extended head each with which to be fitted in the holes of the nozzle holder 97. The nozzle holder 97 is urged by clamps 104 at the lower ends of clamp plates 103 against the bottom of the cylinder block 67, whereby the upper ends of the nozzles are forced in contact with the lower ends of the cylinders 23.

Preferably, an elastic plate such as silicone plate 109 is sandwiched between the nozzle holder 97 and the bottom of the cylinder block 67 to establish airtight communication between the cylinders 23 and the nozzles 99 or 101.

Each clamp plate 103 is supported by the vertical bracket 65 which in turn is held by the horizontal bracket 77, in such manner that the clamp plate can slide vertically along the outer surface of the bracket. A pair of clamp plate guides 105 are fixed to the cylinder block 67 (FIG. 6), and the clamp plate 103 is formed with slots 111 in which the guides 105 fit. A plurality of tension springs 113 are secured at the upper ends to the bracket 65, and the lower ends of the springs 113 are secured to the upper end of the clamp plate 103. As a consequence, the clamp plate 103 is normally biased upward, forcing the nozzle holder 97 against the cylinder block 67 with the aid of the clamps 104 to provide desired airtight communication between the cylinders 23 and nozzles 99 or 101. The strength of the springs 113 can be controlled by adjusting the positions of screws 115.

In conjunction with FIGS. 4 to 6, means for removing the nozzle holder 97 when required will now be explained. Release pins 117 are fixed to each clamp plate 103 and extend through slots formed in the bracket 65 to the inside. As it descends, the plunger plate 91 comes into contact with the release pins 117 and then forces them farther downward against the urgings of the springs 113, and accordingly the clamp plate 103 comes down to release the nozzle holder 97. Thus the nozzle holder 97 descends under its own weight until it rests on holding bends 108 of holder supports 107 secured to the cylinder block 75. In this state the nozzle holder 97 can be horizontally pulled out together with the nozzles 99. This state also allows the nozzle holder to be replaced with another holder of different dimensions.

Next, with reference to FIGS. 4, 7, and 8, means of removing the tips 100 or 102 as needed will be described.

The nozzle holder 97 has stoppers 119 fixed to the four corners of its underside, all in contact with an eject plate 123. The eject plate 123 is elasticly pressed against the stoppers 119 by eject springs 125 held in place by spring pins 121. The plate has throughholes in which the nozzles 99 or 101 extend their lower portions to expose the ends on which tips are to be fitted. For this purpose the lower ends of the throughholes are designed to be smaller in diameter than the upper ends of the tips 100 or 102. Thus, when the eject plate 123 is pushed down, all the tips are dropped off.

Means of pushing down the eject plate 123 may be provided separately, but preferably the clamp plates 103, as in the illustrated Figures, are utilized for that purpose too. The bottom surfaces of the clamps 104 at the lower ends of the clamp plate serve as surfaces to act on the eject plate 123. From the state shown in FIGS. 4 and 6 the clamp plates 103 are forced downward by the descent of the plunger plate 91 to release the nozzle holder 97. As the downward movement continues, the nozzle holder 97 comes to rest on the holding bends 108 of the holder supports 107. A farther descent of the clamp plate causes the clamps 104 to fall past the holding bends 108 to the points shown in FIG. 8. The eject plate 123 then drops away from the stoppers 119 against the urgings of the springs 125, with the consequence that the tips drop off altogether. Subsequent ascent of the plunger plate permits the springs 125 to recover their elasticity to bring the eject plate 123 back to the original position, ready to receive new tips.

As has been described above, the present invention makes it possible to manufacture a liquid dispenser at lower cost than heretofore. Since its plunger-cylinder combinations are made separate from nozzles, and the nozzles are supported by a detachable nozzle holder, not only tips of different sizes can be replaced with ease but also the plunger-cylinder combinations can be used with all sizes of nozzles.

The adoption of an eject plate facilitates the removal of tips.

The use of an elastic seal plate such as of silicone permits airtight coupling of cylinders and nozzle despite the separate nozzle design.

What is claimed is:

1. A liquid dispenser comprising:
   a dispensing head comprising a plurality of plungers supported by a plunger plate, drive means for moving the plunger plate upwardly and downwardly, and a plurality of cylinders in which the plungers slidably fit;
   a plurality of nozzles arranged at lower ends of the cylinders and having configurations adapted to engage airtightly with openings in upper ends of dispensing tips, the plurality of nozzles being supported by a single nozzle holder, which is built to be detachable from said dispensing head; and
   means for attaching and detaching the nozzle holder comprising vertical clamp plates having clamps adapted to be engaged with lower edges of the nozzle holder, elastic members that normally bias the clamp plates upwardly, and means for pressing the clamp plates downwardly against an upward bias of the elastic members.

2. The dispenser according to claim 1, wherein each nozzle has an annular extended head which is adapted to fit in an upper surface of the nozzle holder.

3. The dispenser according to claim 1, wherein said nozzles are self-aligning and fit together with said nozzle holder so there is play therebetween, enabling movement.

4. The dispenser of claim 1, further comprising an elastic seal plate having openings aligned with bores disposed within the nozzles and with the cylinders, wherein said seal plate is sandwiched between an upper surface of the nozzle holder and a lower surface of the cylinders.

5. The dispenser of claim 1, wherein the means for pressing the clamp plates downwardly comprise said plunger plate and means for driving said plunger plate.

6. The dispenser of claim 1, further comprising an eject plate located under the nozzle holder to remove all dispensing tips simultaneously from the nozzles, said eject plate having a plurality of holes formed therein to allow the nozzles to extend therethrough with tip-fitting ends of the nozzles protruding beyond the bottom of the eject plate, a diameter of the holes of the eject plate being smaller than an outside diameter of the upper ends of the dispensing tips.

7. The dispenser of claim 2, wherein said nozzles are self-aligning and fit together with said nozzle holder so there is play therebetween, enabling movement.

8. The dispenser according to claim 2, wherein the means for pressing the clamp plates downwardly comprise said plunger plate and means for driving said plunger plate.

9. The dispenser according to claim 4, wherein the means for pressing the clamp plates downwardly comprise the plunger plate and means for driving said plunger plate.

10. The dispenser according to claim 2, further comprising an eject plate located under the nozzle holder to remove all dispensing tips simultaneously from the nozzles, said eject plate having a plurality of holes formed therein to allow the nozzles to extend therethrough with tip-fitting ends of the nozzles protruding beyond the bottom of the eject plate, the diameter of the holes of the eject plate being smaller than the outside diameter of the upper ends of the dispensing tips.

11. The dispenser according to claim 4, further comprising an eject plate located under the nozzle holder to remove all dispensing tips simultaneously from the nozzles, said eject plate having a plurality of holes formed therein to allow the nozzles to extend therethrough with tip-fitting ends of the nozzles protruding beyond the bottom of the eject plate, the diameter of the holes of the eject plate being smaller than the outside diameter of the upper ends of the dispensing tips.

12. The dispenser according to claim 6, wherein the vertical clamp plates of the means for attaching and detaching the nozzle holder are adapted to engage the eject plate to push down the eject plate when the clamp plates are forced downwardly beyond the nozzle holder.

13. A liquid dispenser comprising:
   a dispensing head comprising:
      a plunger plate;
      a plurality of plungers supported by the plunger plate; and
      a plurality of cylinders having bores in which the plungers slidably fit;
   a drive for moving the plunger plate upwardly and downwardly;
   a holder having an array of holes;
   a clamp for engaging lower edges of the holder;
   elastic members that normally bias the clamp upwardly toward the dispensing head; and
   members coupled to the clamp and engagable by the plunger plate to press the clamp downwardly against an upward bias produced by the elastic members.

14. The liquid dispenser as recited in claim 13 further comprising an elastic seal plate having openings aligned with the bores of the cylinders, the seal plate being disposed between an upper surface of the holder and the cylinders.

15. The liquid dispenser as recited in claim 14 wherein the seal plate is formed of silicone.

\* \* \* \* \*